United States Patent
Davis et al.

(10) Patent No.: US 8,241,588 B2
(45) Date of Patent: Aug. 14, 2012

(54) BINDING ASSAY

(75) Inventors: Paul James Davis, Bedfordshire (GB);
Mark James Davis, Bedfordshire (GB);
Mark Burnapp, Bedfordshire (GB);
Julie Thompson, Northamptonshire (GB)

(73) Assignee: Mologic Ltd, Bedfordshire (GB)

( * ) Notice: Subject to any disclaimer, the term of this patent is extended or adjusted under 35 U.S.C. 154(b) by 264 days.

(21) Appl. No.: 12/280,245

(22) PCT Filed: Feb. 23, 2007

(86) PCT No.: PCT/GB2007/000641
§ 371 (c)(1),
(2), (4) Date: Nov. 6, 2008

(87) PCT Pub. No.: WO2007/096640
PCT Pub. Date: Aug. 30, 2007

(65) Prior Publication Data
US 2009/0098020 A1    Apr. 16, 2009

(30) Foreign Application Priority Data
Feb. 23, 2006  (GB) .................................. 0603666.9

(51) Int. Cl.
*G01N 33/53* (2006.01)
(52) U.S. Cl. ....... 422/420; 422/68.1; 422/430; 422/400; 436/169; 436/518
(58) Field of Classification Search .................... 422/61, 422/68.1, 430, 400, 420; 436/169, 518
See application file for complete search history.

(56) References Cited

U.S. PATENT DOCUMENTS

| | | | |
|---|---|---|---|
| 3,888,629 A | 6/1975 | Bagshawe |
| 4,055,394 A | 10/1977 | Friedman |
| 4,144,306 A | 3/1979 | Figueras et al. |
| 4,178,153 A | 12/1979 | Sodickson et al. |
| 4,258,001 A | 3/1981 | Pierce et al. |
| 4,356,149 A | 10/1982 | Kitajima et al. |

(Continued)

FOREIGN PATENT DOCUMENTS

CA       2569487 A1     12/2005

(Continued)

OTHER PUBLICATIONS

U.S. Appl. No. 12/280,290, filed Aug. 21, 2008, Davis et al.

(Continued)

*Primary Examiner* — Jill Warden
*Assistant Examiner* — Monique Cole
(74) *Attorney, Agent, or Firm* — Clark & Elbing LLP

(57) ABSTRACT

A binding assay product (1) for detecting the presence of an analyte in a sample comprising a labelling module (5), a label, a capture module (9) and a visualization module (10). The labelling module (5) comprises a first binding component capable of binding the analyte. The label is connectable to the first binding component. The capture module (9) comprises a second binding component capable of binding the analyte. The visualization module (10) is for detecting the first binding component connected to the label and bound to the second binding component via the analyte. The labelling module and the capture module comprise a fluid conducting medium in which the binding components are embedded. The labelling module (5), the capture module (9) and the visualization module (10) together define a flow path along which the sample is capable of flowing.

15 Claims, 11 Drawing Sheets

U.S. PATENT DOCUMENTS

| | | | |
|---|---|---|---|
| 4,522,923 A | 6/1985 | Deutsch | |
| 4,604,264 A | 8/1986 | Rothe et al. | |
| 4,689,240 A | 8/1987 | Zweig | |
| 4,703,017 A | 10/1987 | Campbell et al. | |
| 4,727,019 A | 2/1988 | Valkirs et al. | |
| 4,820,489 A | 4/1989 | Rothe et al. | |
| 4,851,356 A | 7/1989 | Canfield | |
| 4,870,005 A | 9/1989 | Akiyoshi et al. | |
| 4,952,520 A | 8/1990 | Okusa et al. | |
| 5,064,770 A | 11/1991 | DeLuca et al. | |
| 5,071,746 A | 12/1991 | Wilk et al. | |
| 5,171,662 A | 12/1992 | Sharma | |
| 5,185,249 A | 2/1993 | Arter et al. | |
| 5,236,826 A | 8/1993 | Marshall | |
| 5,275,785 A * | 1/1994 | May et al. | 422/56 |
| 5,284,622 A | 2/1994 | Krause et al. | |
| 5,296,192 A | 3/1994 | Carroll et al. | |
| 5,565,366 A | 10/1996 | Akers, Jr. | |
| 5,601,986 A | 2/1997 | Takacs | |
| 5,629,164 A | 5/1997 | Rivers | |
| 5,741,659 A | 4/1998 | Ralls et al. | |
| 5,755,231 A | 5/1998 | Krantz et al. | |
| 5,766,961 A | 6/1998 | Pawlak et al. | |
| 5,877,028 A * | 3/1999 | Chandler et al. | 436/514 |
| 5,879,881 A | 3/1999 | Rubenstein | |
| 5,932,410 A | 8/1999 | Whittaker et al. | |
| 6,040,195 A | 3/2000 | Carroll et al. | |
| 6,096,563 A | 8/2000 | Hajizadeh et al. | |
| 6,352,862 B1 | 3/2002 | Davis et al. | |
| 6,686,170 B1 | 2/2004 | Flanders et al. | |
| 6,750,034 B1 | 6/2004 | Darrow et al. | |
| 2003/0207290 A1 | 11/2003 | Kenten et al. | |
| 2003/0211560 A1 | 11/2003 | O'Brien et al. | |
| 2003/0219833 A1 | 11/2003 | Guan et al. | |
| 2004/0029176 A1 | 2/2004 | Yoon | |
| 2004/0038217 A1 | 2/2004 | Yang | |
| 2004/0067168 A1 | 4/2004 | Buffiere et al. | |
| 2004/0096926 A1 | 5/2004 | Packard et al. | |
| 2005/0164311 A1 | 7/2005 | Inglese et al. | |
| 2006/0003394 A1 | 1/2006 | Song | |
| 2006/0234284 A1 | 10/2006 | Yang | |

FOREIGN PATENT DOCUMENTS

| | | | |
|---|---|---|---|
| EP | 0339450 A2 | 11/1989 | |
| EP | 0206075 B1 | 12/1989 | |
| EP | 0158964 B1 | 11/1990 | |
| EP | 0450714 A2 | 10/1991 | |
| EP | 0579250 A2 | 1/1994 | |
| EP | 13942720 A2 | 3/2004 | |
| EP | 2004845 A1 | 7/2004 | |
| EP | 1986779 A1 | 11/2008 | |
| EP | 1989549 A1 | 11/2008 | |
| EP | 1991870 A1 | 11/2008 | |
| FR | 2621393 A1 | 4/1989 | |
| GB | 2259362 A | 3/1993 | |
| GB | 2342993 A | 4/2000 | |
| GB | 2350677 A | 12/2000 | |
| GB | 2410086 A | 7/2005 | |
| JP | 57064160 A | 4/1982 | |
| JP | 2001000197 A | 1/2001 | |
| WO | WO 89/10564 A1 | 11/1989 | |
| WO | WO 91/14000 A1 | 9/1991 | |
| WO | WO 92/15879 A1 | 9/1992 | |
| WO | WO 96/30751 A1 | 10/1996 | |
| WO | WO 96/38727 A1 | 12/1996 | |
| WO | WO 98/00703 A1 | 1/1998 | |
| WO | WO 98/33069 A1 | 7/1998 | |
| WO | WO 98/50778 A1 | 11/1998 | |
| WO | WO 99/67647 A1 | 12/1999 | |
| WO | WO 00/62061 | 10/2000 | |
| WO | WO 00/63700 A1 | 10/2000 | |
| WO | WO 01/25789 A1 | 4/2001 | |
| WO | WO 01/31337 A2 | 5/2001 | |
| WO | WO 03/012443 A2 | 2/2002 | |
| WO | WO 02/35216 A1 | 5/2002 | |
| WO | WO 02/42770 A1 | 5/2002 | |
| WO | WO 02/48674 A2 | 6/2002 | |
| WO | WO 03/058252 A2 | 7/2003 | |
| WO | WO 2004/048935 A3 | 6/2004 | |
| WO | WO 2004/103939 A1 | 12/2004 | |
| WO | WO 2005/005657 A1 | 1/2005 | |
| WO | WO 2005/012558 A1 | 2/2005 | |
| WO | WO 2005/119253 | 12/2005 | |
| WO | WO 2006/006961 A1 | 1/2006 | |
| WO | WO 2007/096637 A1 | 8/2007 | |
| WO | WO 2007/096640 A1 | 8/2007 | |
| WO | WO 2007/096642 A1 | 8/2007 | |
| WO | WO 2007/128980 A1 | 11/2007 | |

OTHER PUBLICATIONS

U.S. Appl. No. 12/280,383, filed Nov. 6, 2008, Davis et al.
U.S. Appl. No. 12/296,413, filed Oct. 7, 2008, Davis et al.
International Search Report (PCT/GB2007/000637) mailed May 25, 2007.
International Search Report (PCT/GB2007/000643) mailed Jun. 1, 2007.
International Search Report (PCT/GB2007/001291) mailed Sep. 14, 2007.
International Preliminary Report on Patentability (PCT/GB2007/000637) mailed Sep. 4, 2008.
International Preliminary Report on Patentability (PCT/GB2007/000643) issued Aug. 26, 2008.
International Preliminary Report on Patentability (PCT/GB2007/001291) issued Oct. 8, 2008.
Written Opinion of the International Searching Authority (PCT/GB2007/000637) completed May 16, 2007.
Written Opinion of the International Searching Authority (PCT/GB2007/000641) completed May 16, 2007.
Written Opinion of the International Searching Authority (PCT/GB2007/000643) completed May 24, 2007.
Written Opinion of the International Searching Authority (PCT/GB2007/001291) completed Aug. 28, 2007.
Anonymous, Quick-Step™ HCG—One Step Urine Pregnancy Test, Internet Citation, XP002423569, 1998.
Camillo Secchi et al., "Monoclonal antibody capture fluorometric enzyme linked immunosorbent assay for detection of porcine growth hormone in plasma," *Analytica Chimica Acta*, 402: 37-45, 1999 (abstract).
International Search Report (PCT/GB2007/000641) mailed Jun. 5, 2007.
International Preliminary Report on Patentability (PCT/GB2007/000641) mailed Sep. 4, 2008.
Office Action from European Patent Application No. 07705272.8, dated Aug. 3, 2009.
Reply to Office Action from European Patent Application No. 07705272.8, dated Dec. 14, 2009.
Office Action from European Patent Application No. 07705272.8, dated Oct. 4, 2010.
Reply to Office Action from European Patent Application No. 07705272.8, dated Dec. 2, 2010.

* cited by examiner 50 mIU/ml    10 mIU/ml    0 mIU/ml

A  B  C  D

BINDING ASSAY

CROSS-REFERENCE TO RELATED APPLICATIONS

This application is the U.S. National Stage of International Application No. PCT/GB2007/000641, filed Feb. 23, 2007, which claims the benefit of GB 0603666.9, filed Feb. 23, 2006.

The present invention relates to a binding assay product and, more specifically, to a binding assay product which comprises means for revealing the binding of first and second binding components, each being part of a specific binding pair, such as an antibody and antigen.

Many types of immunoassay are known in the art for the detection of an analyte in a sample. There are also many different types of devices and architectures, such as the lateral flow (LF) immunoassay system, for conducting various types of immunoassay rapidly and simply. Typically, LF systems comprise a nitrocellulose strip on which are located all of the components needed to complete an assay. Usually there is a first monoclonal antibody linked to a tracer label (such as gold particles) and a second monoclonal antibody immobilised in a discrete region of the test strip, to form a capture band. The first antibody (with binding specificity for one epitope of the analyte to be detected) is present in a fixed amount, complete with the corresponding label substance, in a location (the labelling band) and condition such that it can be taken up by any incoming fluid before the fluid reaches a capture band. The capture band comprises a defined quantity of the second monoclonal antibody, which is specific for a second, spatially distinct epitope of the same analyte.

In use, a fluid sample is applied to one end of the strip in sufficient quantity to enable the sample to flow along the strip, firstly interacting with and mobilising the tracer-labelled first antibody. Any analyte molecules present in the sample bind to the first antibody as the mixture of sample and mobilised tracer labelled antibodies move toward the capture band. Analyte molecules that have bound the tracer antibodies by the first epitope then bind to the second antibodies immobilised in the capture band, by the spatially distinct second epitope. Thus the label becomes immobilised at the capture band. When the label substance is in the form of gold particles, the accumulation of gold particles in the capture band provides a visible band which may be observed by a user as an indication of the presence of the analyte in the sample. If, on the other hand, the analyte is not in the sample then the tracer labelled antibody passes through the capture band and no visible line forms on the strip.

In some versions of the lateral flow immunoassay, a control band is also provided, which comprises a defined quantity of immobilised antibodies specific for tracer-labelled antibody. The control band is located on the far side of the capture band. Thus, when the labelled antibody passes through the capture band, it becomes immobilised in the control band and a visible line forms. In practice, some labelled antibody passes through the capture band whether or not analyte is present in the sample and so the presence of a visible line at the control band is indicative that the assay has run its course (which may not occur, for example, if there is insufficient fluid in the sample). The control band may, in some arrangements of the system, provide a useful visual comparison between the control band and the capture band.

The use of this type of lateral flow immunoassay product is well established, for example, in pregnancy testing kits, where the analyte in question is hCG (human chorionic gonadotropin) which may be detected in a sample of, for example, urine from an individual.

An LF immunoassay is easy to use but there are number of ways in which improvements would be desirable. For example, the potential to construct compact versions of LF devices is severely limited because of the need to make samples run through defined distances of test strip. These internal strip dimensions are crucial to performance of the test, for the correct reaction times in LF have to be achieved by providing a linear zone along which the reaction mixture (sample plus mobile reagents) must flow. The duration of this linear flow stage determines the timing of the crucial molecular interactions on which the test depends. In other words, assay stage timings are equivalent to the physical length of the device. If a longer reaction time is needed, it is necessary to increase the length of the test strip.

In practice, virtually all commercial LF assay units have become fixed into a particular design idiom. For example, the general shape and dimensions of a home pregnancy test (which are almost always some form of LF immunoassay) are universally recognised. In the context of home pregnancy testing this is not a problem, as the basic design limitations of LF do not conflict with this particular use but in other types of application, the standard format may not be ideal. For example, when a test system has to work quantitatively by interfacing with computers, or by insertion into a simple reader, the format constraints can become a problem. Even in the field of pregnancy tests and fertility monitoring, it would be desirable to produce test systems that look and handle differently, and this requires wide-ranging design changes.

A less widely used immunoassay format is known as "vertical flow immunoassay". Such immunoassays comprise a capture zone, which may be in the form of a nitrocellulose membrane on which are immobilised a plurality of monoclonal antibodies which are each specific for one epitope of the analyte. In this respect, the antibodies approximately correspond to the antibodies of the capture zone of the lateral flow immunoassay.

In use, the sample is deposited onto the nitrocellulose membrane and any analyte present in the sample binds to the immobilised antibodies. The sample is then washed off or through the membrane in order to remove any unbound constituents. Subsequently, labelled antibody is applied to the substrate. The labelled antibody is specific for another epitope of the analyte and has a label, such as a gold particle, conjugated to it. In this respect, the labelled antibody approximately corresponds to the labelled antibody delivered from the labelling band of the lateral flow immunoassay. If analyte is present on the membrane bound to the immobilised antibodies, then the labelled antibodies bind to the analyte as well.

The membrane is then washed again to remove any unbound labelled antibody. If labelled antibody remains on the membrane, then this is indicative of the presence of the analyte in the sample. The absence of labelled antibody on the membrane after the wash step is, on the other hand, indicative of the absence of analyte in the sample.

One of the advantages of the "vertical flow" immunoassay is that it can be smaller than a lateral immunoassay. Moreover, it can be made to work with more difficult samples (e.g. with variable viscosity, or complex contaminants). However, the problem is that it requires several procedural steps, making it more complicated to operate, particularly for an unskilled person.

Despite the success of both lateral flow immunoassays and vertical flow immunoassays, there are several drawbacks with one or both of the assays.

In some situations, the lateral flow immunoassay suffers from the problem that it can be difficult to observe the line at the capture band because it is comparatively thin, and can form in a non-uniform manner (with a distinct leading edge and trailing edge of different intensities). Thus it can be difficult for users of a lateral flow immunoassay to detect the presence of a faint line at the capture band.

Another problem with the lateral flow immunoassay is that the flow of fluid across a nitrocellulose strip can be variable. The speed of flow of the sample fluid to the end of the strip effectively dictates the length of time for which the assay runs. Consequently, any variability in flow rate (e.g. caused by inconsistencies in the casting process) results in variability in the length of time for which an assay will run on a lateral flow immunoassay strip. Thus in order to ensure that the assay continues for at least the minimum required length of time, a lateral flow immunoassay strip needs to be relatively long. Accordingly, there is a general problem of managing the flow of fluid along a lateral flow immunoassay strip and the more specific problem of the size of lateral flow immunoassay strips.

A further problem with known vertical flow immunoassay products is that they are inherently open to the environment. This is particularly a problem for flow-through immuno assay kits, where the substrate must be exposed in order to permit the sequential depositing and washing steps.

The present invention seeks to alleviate one or more of the above problems.

According to one aspect of the present invention, there is provided a binding assay product for detecting the presence of an analyte in a sample comprising:

a labelling module comprising at least one first binding component capable of binding the analyte;

a label connectable to the first binding component;

a capture module comprising at least one second binding component capable of binding the analyte; and a visualisation module for detecting the first binding component connected to the label and bound to the second binding component via the analyte.

Conveniently, at least the labelling module and the capture module each comprise a fluid conducting medium in which the first and second binding components are embedded Preferably, the labelling module, the capture module and the visualisation module together define a flow path, along which a sample is capable of flowing.

Advantageously, the binding assay product further comprises at least one barrier along the flow path, the barrier being capable of slowing the progress of the sample along the flow path.

Conveniently, the barrier is soluble in water.

Preferably, the at least one barrier interposes between the labelling module and the capture module and/or between the capture module and the visualisation module.

Advantageously, the visualisation module comprises a porous material to which the binding products are retained in the presence of an analyte.

Conveniently, the label is connected to the first binding component.

Alternatively, the label and the first binding component each comprise one of a binding pair.

Preferably, the binding pair are avidin and biotin.

Advantageously, the binding assay product further comprises a mixing module, on the flow path, between the labelling module and the capture module.

Conveniently, the binding assay product according to any one of the preceding claims and further comprises a sample receiving module on the flow path comprising an absorbent material in fluid communication with the labelling module.

Preferably, the binding assay product further comprises a sump on the flow path, the sump comprising an absorbent material in fluid communication with the visualisation module.

Advantageously, the visualisation module comprises the boundary between the capture module and the sump.

Conveniently, the sump comprises a material which prevents the passage therethrough of components having a size above a threshold size.

Preferably, the binding assay product further comprises a casing around the labelling module, the capture module and the visualisation module.

Advantageously, the binding assay product further comprises a supply of a wash fluid.

Conveniently, the flow path is non-linear.

Preferably, the flow path is generally "U-shaped".

Advantageously, the visualisation module is located at a point on the flow path where the flow path changes direction.

Conveniently, the visualisation module comprises a blister which protrudes from the rest of the binding assay product.

Preferably, the first and second binding components are antibodies or antigen-binding fragments thereof.

Advantageously, the longest dimension of the binding assay product is less than 3 cm long.

Conveniently, the modules of the binding assay product are interchangeably connected to each other.

According to a further aspect of the present invention, there is provided a kit for making a binding assay product according to the invention, the kit comprising the labelling module, the capture module and the visualisation module, the modules being interchangeably connectable with each other to form the flow path In another aspect of the present invention there is provided a means (a device) for conducting a vertical flow binding assay, such as an immunoassay, automatically, simply by applying a liquid test sample to a sample inlet zone or member, and allowing the sample to flow vertically through one or more assay stages housed in discrete but connected open-porous structures. Wherein the transit of the sample through the device is temporarily interrupted by at least one soluble barrier interposed between two of the open-porous structures. The barrier may be in the form of a dried film of water-soluble polymer (such as polyvinyl alcohol), which must be dissolved before the sample can resume its progress through the fluid path of the assay. A capture module or zone is provided in the form of a membrane, disc or pad through which test sample is made to flow vertically rather then laterally (i.e. through its narrowest axis, rather than along its longest axis), downstream of at least one open porous structure and a soluble barrier film. This ensures that the sample can only reach the capture zone after it has been in contact with a defined amount of tracer-labelled reagent (at least) for a sufficient period of time, as controlled by the soluble barrier. The capture zone carries immobilised binding molecules (e.g. antibodies) and is in fluid contact with a sump into which sample and excess reagent is gathered, thus ensuring a steady, even flow through the pores of the capture zone.

The capture zone also acts as a display or signal-gathering area. It can be formed from a thin layer of particles (e.g. Sepharose bearing streptavidin) sandwiched between the sump and an upstream porous block forming part of the fluid path. Even if the device is of a cylindrical construction, the colour of the Sepharose layer can be clearly viewed from the side, and the optical path through the Sepharose layer enables efficient visual detection. The soluble barrier or dam film(s) are responsible for controlling the timing of the assay steps, as the fluid (i.e. sample plus reactant) is not able to enter the next zone or module until the film has dissolved to open the fluid path.

It will be appreciated that this differs from a LF device in many important ways, including the nature of the carrier materials and the way the reactants are disposed in relation to the capture/display visualisation zone, as well as the nature of the capture/display visualisation zone itself. The soluble dam feature is, of course, unique. All of these features, either individually or in unison, bring about the set of advantages and benefits, as described earlier.

The modular nature of the structure allows for more complex assay sequences to be embodied with great ease. Different reaction sequences can be constructed by the order in which the modules are inserted into the device. For example an extra binding partner (such as an avidin conjugate) can be dried in a porous zone and included before or after the main antibody-antigen binding zone. The ability to make these modules from sheets of porous matrix means that complete devices can be manufactured in reel-to-reel processes. Individual devices can then be cut from such laminated composite multi-layers. The carrier matrices can be made from open porous materials, which will allow viscous fluids to pass through easily. This open porosity results in very short residence times, as the sample and reagents travel toward the capture zone, but the rate of flow and step-timing (i.e. residence time) are controlled by the soluble dam sheets.

Soluble barrier or dam films or sheets offer great advantages, and they can be made from a wide variety of substances. It is possible to use commercially available soluble films marketed as "mouth freshening films" (e.g. by Listerine™). These are loaded with flavour/fragrance molecules and are constructed from water soluble polymers. Although brittle, they have near to ideal properties as soluble dams with which to control flow in VFI experiments. Variations in timing can be achieved by adding extra layers into a single dam. A dam made from 2 layers will hold back the flow for almost twice as long a time as a dam made from 1 layer. Especially suitable soluble films can be made from PVA and other known polymers, and these can be used to carry and deliver assay reagents into the assay mixture at defined points, as well as acting as barriers. For example, enzymes and substrates can be incorporated into film formulations, wherein they are found to be very stable. As the film dissolves, so the entrained reagents are released to react with the sample and other reagents. Such films are available from, for example Biofilm Ltd, based in Hamilton, near Glasgow (http://www.biofilm.co.uk).

The use of soluble dams working with open pore fluid-handling structures allows for very wide sample compatibility, without loss of control of crucial assay timings. Rinse fluids can be used very effectively in such open pore structures, and the modular assembly approach can allow rinse fluids to be easily incorporated. The capture/detection/reading/visualisation zone can be embodied in a large number of ways, from trapped particle layers to thin membranes; a versatility which can be used to great effect in designing alternative detection systems or device architectures (e.g. allowing the efficient use of electrodes for electrochemical detection).

In order that the present invention may be more readily understood and so that further details thereof may be appreciated, embodiments of the invention will now be described, by way of example, with reference to the accompanying drawings in which.

Figure 1:
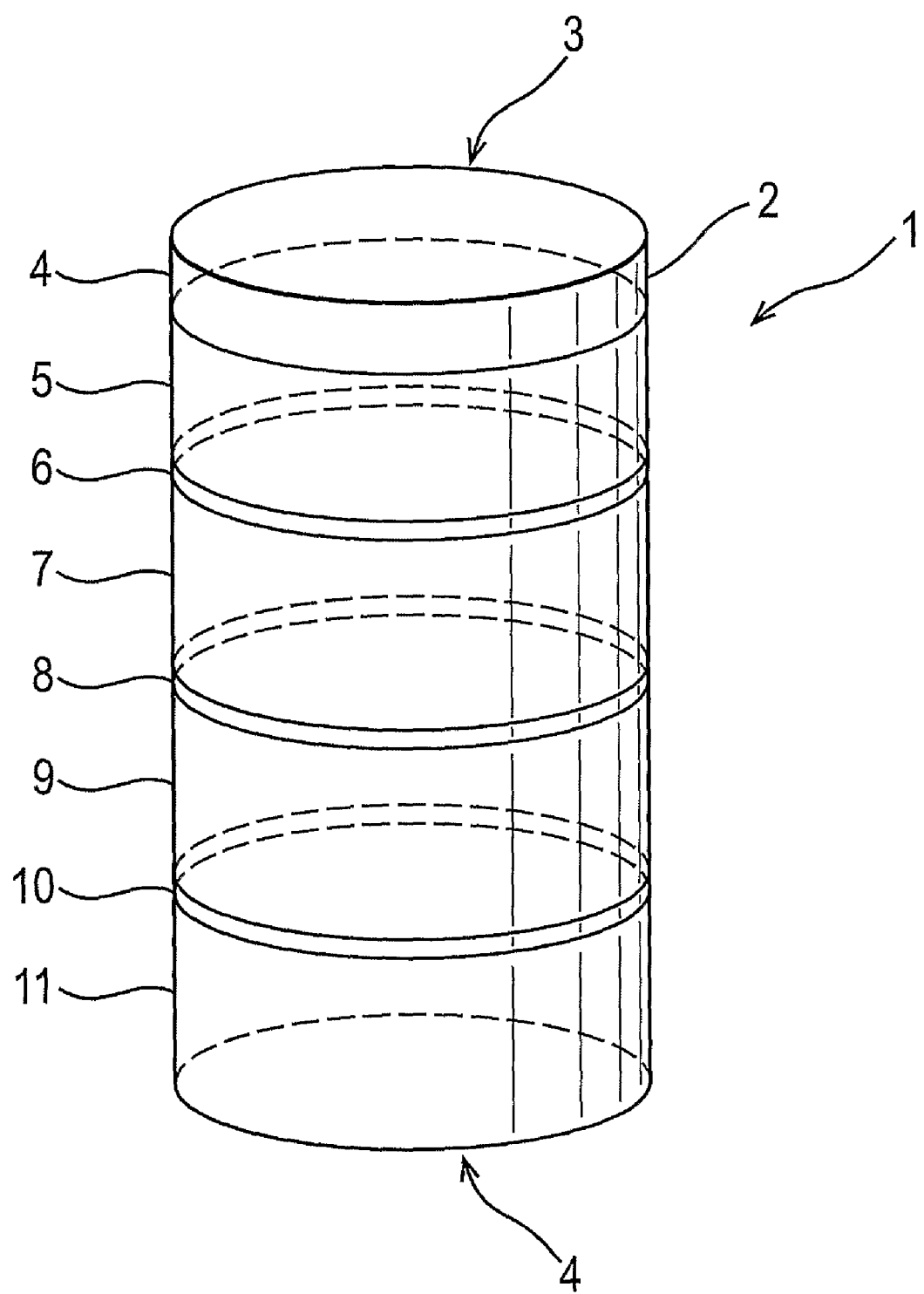
FIG. 1 is a perspective view of a binding assay product in accordance with one embodiment of the present invention.

Referring to FIG. 1, a binding assay product 1 comprises a transparent cylindrical casing 2 made from a plastics material. The casing 2 is open at a first end 3 but is closed at a second end 4

Contained within the casing 2, at the first end 3, is a sample receiving disc 4, which is made from an absorbent material.

Beneath the sample receiving disc 4, away from the open end 3, is provided a labelled antibody disc 5. The labelled antibody disc 5 comprises a disc made from a fluid conducting medium such as sintered plastic rendered hydrophilic by plasma treatment in which are embedded a plurality of monoclonal antibodies, each specific for one epitope of an analyte. Such a plastic is available from Porvair Ltd under the trade name Porvair. Conjugated to each of the monoclonal antibodies is a visible label (e.g. gold particle).

Beneath the labelled antibody disc 5 is provided a disc-shaped first soluble barrier 6. The first soluble barrier 6 is made from a material such as low MW polyvinyl alcohol (PVA) or water soluble gelatine (e.g. fish gelatin). Its thickness is selected such that it is impermeable to water for a predetermined length of time but after this period of time, in the presence of water, the first soluble barrier 6 is dissolved and permits fluid flow. In order to make the first soluble barrier 6, the polymer (e.g. PVA) is dissolved in water to about 5% w/v and spread into a flat dish. Water is removed by drying at about 40° centigrade, preferable under moving air. Alternatively, drying is achieved by irradiating the solution with infra red radiation in the presence of moving air. Optionally, glycerol or propylene glycol are included at about 2-5% (v/v) to keep the film flexible when the water has been removed.

Beneath the first barrier 6 is provided a mixing disc 7 made from a fluid conducting medium such as glass fibre.

Beneath the mixing disc 7 is provided a second soluble barrier 8 which is substantially identical to the first soluble barrier 6, although it may be of a different thickness so as to become permeable in the presence of water after a different length of time from the first soluble barrier 6.

Beneath the second soluble barrier 8 is located a capture antibody disc 9 which comprises a fluid-conducting medium such as packed sepharose particles in which are embedded a plurality of monoclonal antibodies to another epitope of the analyte. Each of the capture antibodies is conjugated to a sepharose particle.

Beneath the capture antibody disc 9, is provided a disc-shaped selective membrane 10. The selective membrane 10 contains a large number of pores of a threshold size, which are large enough to permit the passage of the labelled antibody but which are too small to permit the passage of the sepharose particle, which is conjugated to the capture antibody.

Beneath the selective membrane 10 is provided a disc-shaped absorbent sump 11. The absorbent sump 11 sits against the closed end 4 of the casing 2. The absorbent sump 11 is made from a material such as Porvair™.

It is to be appreciated that the first and second soluble barriers 6, 8 and the selective membrane 10 ensure that the labelled antibodies and the capture antibodies remain in their respective discs 5, 9, before the binding assay product 1 is used.

It is also to be appreciated that, once the soluble barriers 6, 8 have dissolved, the sample receiving disc 4, the labelled antibody disc 5, the mixing disc 7, the capture antibody disc 9 and the absorbent sump 11 define a liquid flow path through which a liquid may be absorbed.

In use, an aqueous sample in which it is desired to detect the presence of the analyte is deposited on the sample receiving disc 4, via the open end 3 of the casing 2. The fluid in the sample is absorbed into the sample receiving disc 4 and then into the labelled antibody disc 5. When the sample reaches the first soluble barrier 6, it is halted, since the barrier is initially impermeable, but the water in the sample begins to dissolve the first soluble barrier 6 and penetrates the first soluble barrier 6 after a predetermined period of time, for example, 2 minutes. During this period of time, the sample is thoroughly absorbed by the labelled antibody disc 5.

Once the first soluble barrier 6 becomes permeable, the sample, mixed with the labelled antibodies is absorbed into the mixing disc 7. When the mixture of the sample and the labelled antibodies reaches the second soluble barrier 8, it is halted because the second soluble barrier 8 is initially impermeable. However, the water in the sample dissolves the second soluble barrier 8 after a predetermined length of time, for example 2 minutes. During this period of time, the labelled antibody binds to any analyte present in the sample.

Once the second soluble barrier 8 has been dissolved, the mixture of the sample and the labelled antibody is absorbed into the capture antibody disc 9. Any analyte in the sample binds to the capture antibodies. More specifically, each analyte molecule is bound both to a labelled antibody (which it is bound in the mixing disc 7) as well as to a capture antibody. Thus each analyte molecule acts as a link or bridge between a labelled antibody and a capture antibody.

As the mixture of sample, labelled antibody and capture antibody reaches the selective membrane 10, the capture antibody is prevented from passing through the membrane, due the size of the sepharose particle to which it is conjugated. Furthermore, any labelled antibody which is bound to the capture antibody via the analyte is also prevented from passing through the selective membrane 10 for the same reason. However, any unbound labelled antibody passes through the selective membrane 10 and into the sump 11.

Consequently, if there is no analyte in the sample then the labelled antibody passes all of the way through the binding assay product 1, into the absorbent sump 11 and is dispersed therein being effectively invisible. If, on the other hand, the analyte is present in the sample then the analyte binds to both the labelled antibody and the capture antibody and the labelled antibody thus becomes immobilised at the selective barrier 10 because of the sepharose particle bound to each capture antibody. Thus the labelled antibody accumulates in a small, disc-shaped volume and the gold particle provided on the labelled antibodies is visible to an observer. The presence of a visible disc at the selective membrane 10, after completion of the assay, is thus indicative of the presence of the analyte in the sample. The disc which forms at the selective membrane 10 is readily visible because it stretches across the entire breadth of the casing 2.

It is to be appreciated that the selective membrane 10 therefore acts as a visualisation zone which is indicative of the outcome of the assay. The presence of a visible disc at this visualisation zone indicates the presence of the analyte in the sample whereas the absence of a visible disc at the visualisation zone indicates the absence of the analyte in the sample.

It is also to be noted that each of the sample receiving disc 4, the labelled antibody disc 5, the first soluble barrier 6, the mixing disc 7, the second soluble barrier 8, the capture antibody disc 9, the selective membrane 10 and the absorbent sump 11 are effectively independent modules. Modules can be added, moved or removed with ease in order to generate a binding assay product with a different arrangement of modules.

Figure 2:
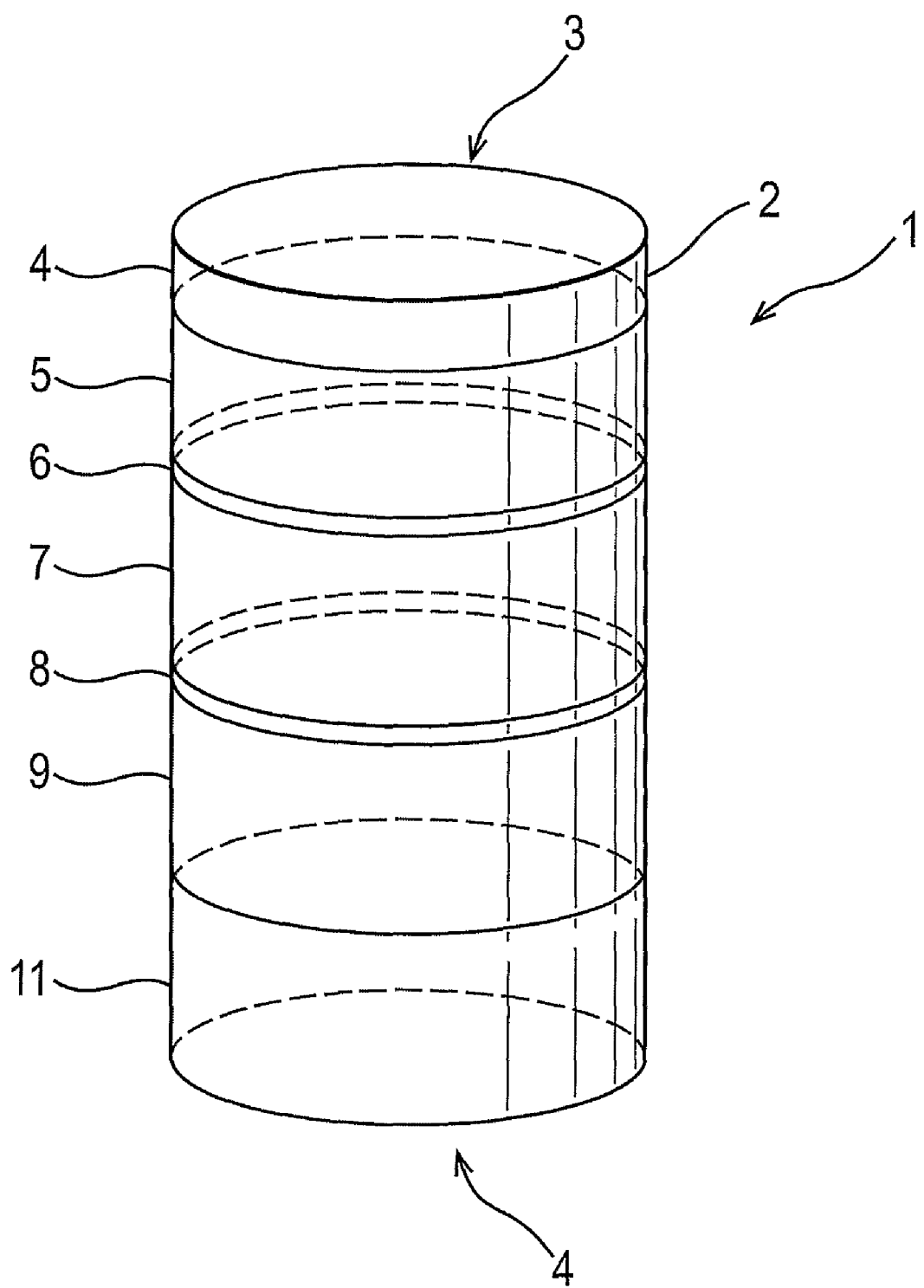
FIG. 2 is a perspective view of a binding assay product according to a further embodiment of the present invention.

Referring, now, to FIG. 2, a second embodiment of the present invention is shown, which is similar to the first embodiment and like components are given the same reference numerals. Thus a binding assay product 1 comprises a cylindrical casing 2 which contains, in sequence from an open first end 3: a sample receiving disc 4, a labelled antibody disc 5, a first soluble barrier 6, a mixing disc 7, a second soluble barrier 8 and a capture antibody disc 9. However, in this second embodiment, the selective membrane 10 is not provided. Instead, the absorbent sump 11 is provided directly adjacent to and beneath the capture antibody disc 9. The absorbent sump 11 is made from a material such as Porvair™ which is permeable to molecules beneath a threshold size but is impermeable to molecules above the threshold size. The sepharose particle to which the capture antibodies are conjugated being bigger than the threshold size, but the labelled antibodies are smaller than the threshold size. For example, in some embodiments the absorbent sump 11 is made from Porvair sintered plastic with a pore size of about 10-90 microns.

In use, an aqueous sample which it is desired to determine the presence of an analyte is deposited on the sample receiving disc 4 and passes from there through the labelled antibody disc 5, the first soluble barrier 6, the mixing disc 7, the second soluble barrier 8 and the capture antibody disc 9, as in the previous embodiment. If there is no analyte in the sample then the labelled antibody passes into the absorbent sump 11 and is dispersed therein, being effectively invisible.

If, however, analyte is present in the sample then the analyte binds both to the labelled antibodies and to the capture antibodies and the resulting complexes become immobilised at the boundary between the capture antibody disc 9 and the absorbent sump 11. This is because the complexes are too big, due to the presence of the sepharose particle, to enter the absorbent sump 11. The accumulation of the labelled antibodies at the boundary results in the gold particles forming a visible disc which may be observed by a user of the binding assay product 1.

Thus, in this embodiment, the boundary between the capture antibody disc 9 and the absorbent sump 11 corresponds to the visualisation zone.

Figure 3:
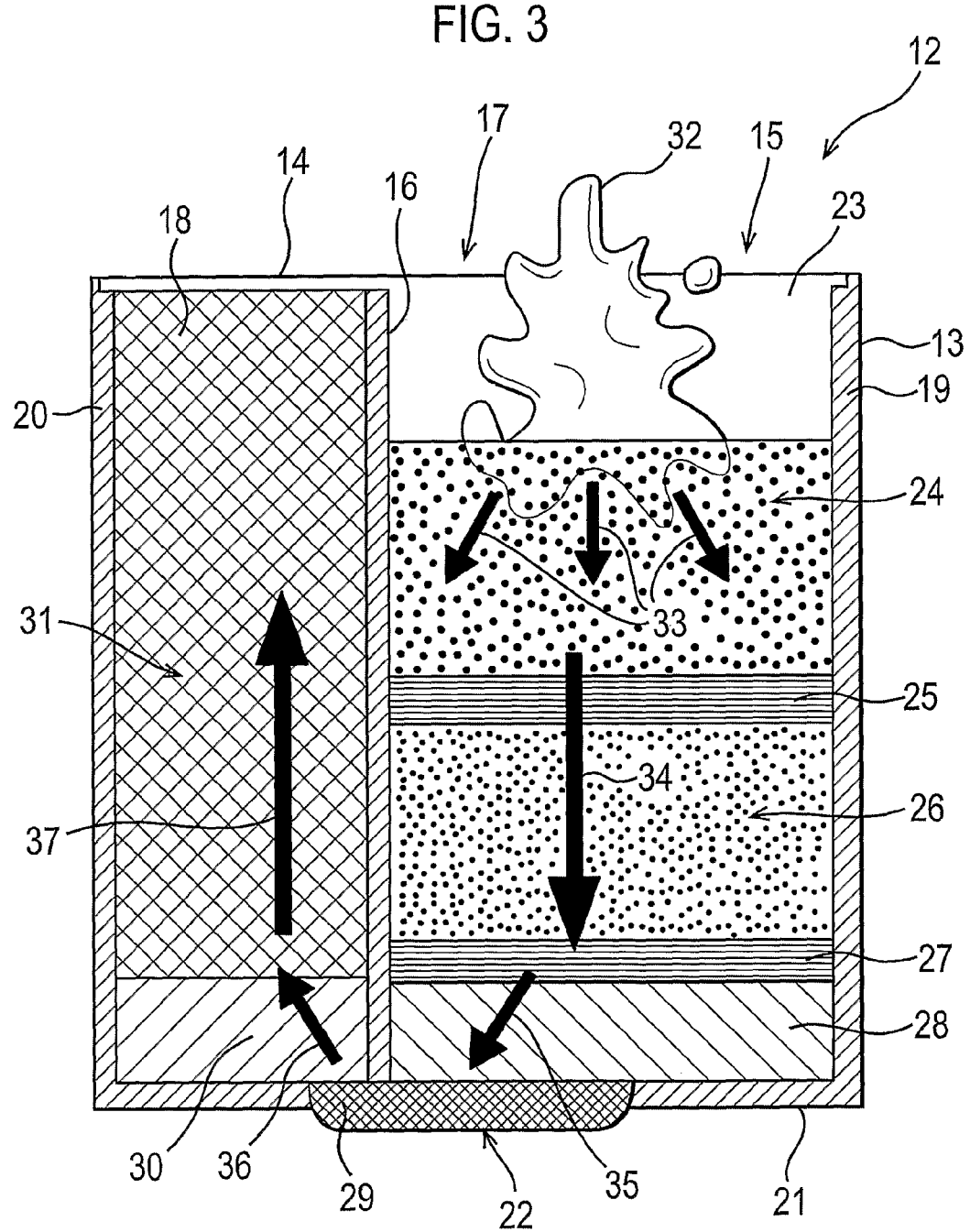
FIG. 3 is a cross-sectional view of a binding assay product in accordance with another embodiment of the present invention.

Referring now to FIG. 3, a cross-sectional view of a third embodiment of the present invention is shown. In the third embodiment, a binding assay product 12 comprises a generally cuboidal casing 13. At one side 14 of the casing 13, an aperture 15 is provided in the casing 13, extending approximately two-thirds of the way along the side 14. Extending inwardly of the aperture 15 is provided an interior wall 16 which separates first and second channels 17, 18 within the casing 13, from each other. Thus, the first channel 17 is defined by the wall 16 and a second side 19 of the casing 13, the second side 19 being perpendicular to the first side 14. The second channel 18 is defined by the internal wall 16 and a third side 20 of the casing 13 which is parallel to the second side 19. Thus the first and second channels 17 or 18 are parallel to each other.

The casing also comprises a fourth side 21 which is parallel to the first side 14 and perpendicular to the second and third sides 19, 20. In the centre of the fourth side 21 is provided a transparent blister 22 which extends outwardly from the fourth side 21 and separates the fourth side 21 from the interior wall 16 so as to provide a passage from the first channel 17 to the second channel 18.

In the first channel 17, adjacent to the aperture 15 in the casing 13, there is provided a recess 23, for receiving a sample. At the bottom of the recess is provided a labelling antibody block 24. The labelling antibody block 24 comprises a block of a fluid conducting medium to prevent passage of Sepharose particles. Thus the afferent block 28 and the efferent block 30 permit fluid communication and from the captive antibody block 29 while keeping the Sepharose particles of the capture antibody block 29 in place in which are embedded a plurality of monoclonal antibodies, each specific for one epitope of an analyte. Each labelling antibody is conjugated to a biotin molecule.

At the bottom of the labelling antibody block 24 is provided a first soluble barrier 25 made from a material dissolvable in water. The first soluble barrier 25 extends completely across the width of the first channel 17 and thus provides an impermeable barrier until it is dissolved. Dried into the soluble barrier 25 is a plurality of gold particles, each gold particle being coupled to a plurality of avidin molecules.

Beneath the first soluble barrier 25, is provided a mixing block 26, also made from a fluid conducting medium. Beneath the mixing block 26 is provided a second soluble barrier 27 which is substantially identical to the first soluble barrier 25 except that no gold particles are dried within it. Furthermore, the thickness of the second soluble barrier layer 27 may be different from the thickness of the first soluble barrier 25 so that it dissolves after a different length of time.

Beneath the second barrier 27 is an afferent block 28 made from a fluid conducting medium. The afferent block 28 lies adjacent to the fourth side 21 of the casing 13 and also adjacent to a first portion of the blister 22. The blister 22 contains a capture antibody block 29. The capture antibody block 29 comprises a fluid conducting medium made from packed Sepharose particles in which are embedded a plurality of monoclonal antibodies specific to another epitope of the analyte, each of the capture antibodies being immobilised in the capture antibody block 29.

At the bottom of the second channel 18, and thus adjacent the fourth wall 21 and the blister 22 containing the capture antibody block 29, is provided an efferent block 30 made from a fluid conducting medium. The afferent block 28 and the efferent block 30 are each made from a medium having a pore size that is large enough to allow the passage of the labelling antibodies and gold particles (e.g 50 nm gold particles) but small enough to prevent passage of Sepharose particles. Thus the afferent block 28 and the efferent block 30 permit fluid communication to and from the capture antibody block 29 while keeping the Sepharose particles of the capture antibody block 29 in place.

The blister 22 extends across the interior wall 16 and thus the capture antibody block 29 fills the passage that lies between the first channel 17 and the second channel 18.

Thus the afferent block 28 is in fluid communication with the capture antibody block 29 which is, in turn, in fluid communication with the efferent block 30.

Above the efferent block 30 is provided an absorbent sump 31, which extends into the remainder of the second channel 18, up to the first side 14.

It is to be appreciated that, once the soluble barriers 25, 27 are dissolved, the labelling antibody block 24, the mixing block 26, the afferent block 28, the capture antibody block 29, the efferent block 30 and the absorbent sump 31 define a liquid flow path along which a liquid may be absorbed. Unlike the first and second embodiments, in this embodiment, the liquid flow path is non-linear, since it is substantially "U-shaped" as it flows downwardly through the first channel 17, then changes direction in the blister 20 and then goes upwardly in the second channel 18. The blister 22 is thus located at a point on the flow path where the flow path changes direction.

In some variants of this embodiment, the first aperture 15 is covered by a foil wrapper (not shown).

The same types of material may be used to construct the components of the third embodiment as in the previous embodiments.

In order to detect the presence of an analyte in an aqueous sample, the binding assay product 12 is used as follows.

If a foil wrapper is provided on the binding assay product 12 then this is removed in order to reveal the recess 23. The sample 32 is deposited into the recess 23 and is then absorbed into the labelling block 24 in the direction of the arrows 33. When the sample 32 reaches the first barrier 25, it is halted as the first soluble barrier 25 is initially impermeable.

After a period of time, the water in the sample 32 dissolves the first soluble barrier 25, allowing fluid flow through it. During this period of time, the sample thoroughly mixes with the labelling antibody and, as the first soluble barrier 25 dissolves, there is further mixing with the gold particles. This mixing results in the binding of the labelling antibodies to the gold particles, via a biotin-avidin bond.

The mixture of components is then absorbed into the mixing block 26, in the direction of the arrow 34. When the mixture of components reaches the second soluble barrier 27, it is again, halted, since the second soluble barrier layer is initially impermeable. After a period of time, however, the water in the sample 32 dissolves the second soluble barrier 27, at which point the second soluble barrier 27 becomes permeable. During this period of time, thorough mixing of the sample 32 with the labelling antibody and the gold particles takes place, ensuring that any analyte in the sample binds to the labelling antibody and the labelling antibody binds to the gold particle via an avidin-biotin bond.

The mixture of components then passes through the afferent block 28 in the direction of the arrow 35.

Subsequently, the mixture of components enters the blister 22, which contains the capture antibody block 29. The capture antibodies bind to any analyte that is present in the sample 32. Thus if analyte is present in the sample 32 then a complex forms of the gold particle, the labelling antibody, the analyte and the capture antibody, with the analyte providing a link or bridge between the labelling antibody and the capture antibody.

The sample is absorbed into the efferent block 30. The mixture then passes into the absorbent sump 31 in the direction of the arrows 36, 37.

Thus if no analyte is present in the sample 32 then the labelling antibodies pass through the first channel 17, through the blister 22, through the second channel 18 and into the absorbent sump 31, where they are dispersed. If, on the other hand, the analyte is present in the sample 32 then the analyte binds to the labelling antibody and to the capture antibody in the capture antibody block 29. The labelling antibody thus becomes immobilised and accumulates within the blister 22. Since the labelling antibody is coupled to gold particles, the gold particles thus also accumulate in the blister 22 and are visible in the blister 22. Thus, in this embodiment, the capture antibody block 29 in the blister 22 forms the visualisation zone, which is indicative of the presence of the analyte in the sample, once the assay has been completed.

It is to be understood that the first and second soluble barriers 25, 27 of this embodiment may be produced by punching out appropriately discs from a sheet of a suitable material. It is also to be noted that the advantage of having the gold particles initially separate from the labelling antibodies is that large numbers of the first soluble barrier 25 can be produced, having gold particles dried into them, irrespective of the analyte to be detected. The first soluble barriers 25 can be incorporated into a range of binding assay products for the detection of different analytes.

It is to be appreciated that, since the above described embodiments have large visualisation zones extending in two dimensions, they are readily visible to an observer.

Furthermore, since the above described embodiments have a sample flow path which is interrupted by soluble barriers, the flow rate of the sample is defined not by the length of the flow path but instead by the time taken for the soluble barriers to dissolve. Moreover, since the binding assay product is encased in a casing, it is generally enclosed from the environment. Indeed, these two features of the above-described embodiments mean that the binding assay products can be miniaturised to a size (e.g. less than 3 cm in length) where they may be swallowed by an individual, the assay taking place within the body of the individual. The miniaturised product may be operated remotely, for example in the lumen of the colon.

In alternative embodiments of the present invention, it is to be appreciated that the soluble barriers described in the previous embodiments may be substituted with barriers which are selective in terms of the pore size of components passing therethrough. In such alternative embodiments, the flow rate of the sample through the binding assay product is dependent upon the size of the components in the sample.

In a variant of the embodiments depicted in FIGS. 1 to 3, a cap is provided over the open end 3 (FIGS. 1 and 2) or the aperture 15 (FIG. 3). The cap contains a small tank with a frangible lid. The tank is filled with a wash fluid. A sharp edge protrudes from the open end 3 or aperture 15 in proximity to the frangible lid. In order to use the binding assay product of these embodiments, the cap is first removed from the casing 2, 13 and the sample is deposited in the binding assay product 1, 12, as in the above-described embodiments. Subsequently, the cap is returned to the rest of the binding assay product 1, 12 and the lid of the cap is broken, by pressing down hard on the cap such that the sharp edge punctures the frangible lid. This releases the wash fluid to follow the sample through the flow path. These embodiments ensure that there is sufficient fluid in the assay to carry the sample all the way through the liquid flow path to the absorbent sump 11, 31.

Although the above descried embodiments comprise antibodies which bind the analyte in the sample (i.e. they are immunoassays) the present invention is not limited to the use of antibodies. For example, in some alternative embodiments lectin proteins are used to bind a carbohydrate moiety on the analyte.

EXAMPLES

Example 1

Reagent Deposition into Frits Material

Reagents specific to an hCG (human chorionic gonadotrophin) immunoassay (antibodies and particles) were dried into Porvair filters made from sintered PE (and known as "frits") and then reconstituted to assess that they retained specific activity for their analyte. One antibody reagent was labelled with gold sol and a second was simply biotinylated. 20 µl of diluted reagent was dosed onto HP filters and air dried at room temperature.

Figure 4:
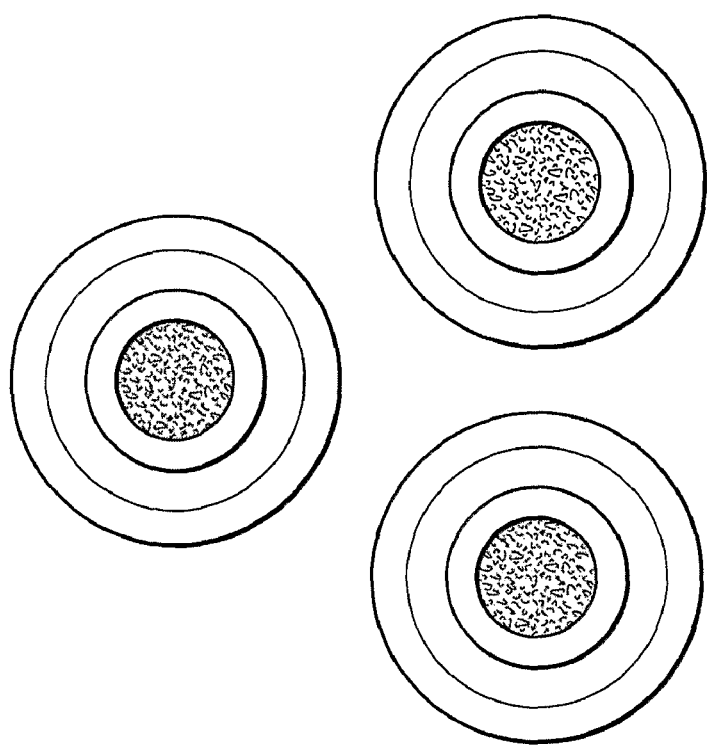
FIG. 4 shows a plan view of three modules from a binding assay product according to one embodiment of the present invention.
Figure 5:
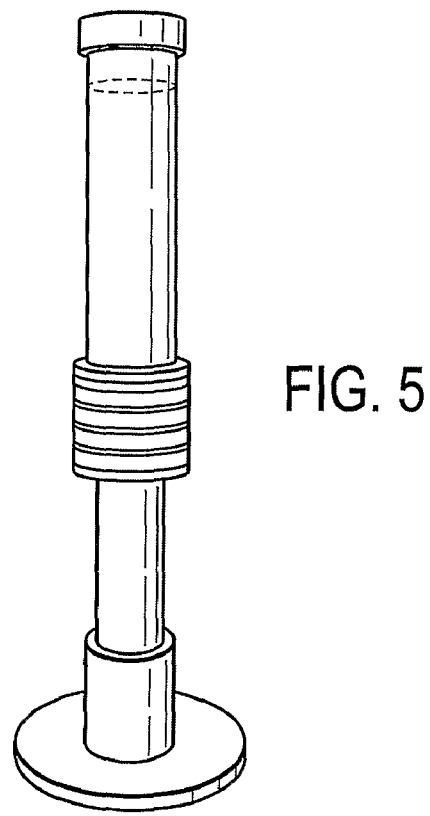
FIG. 5 shows a side view of a binding assay product according to another embodiment.
Figure 6:
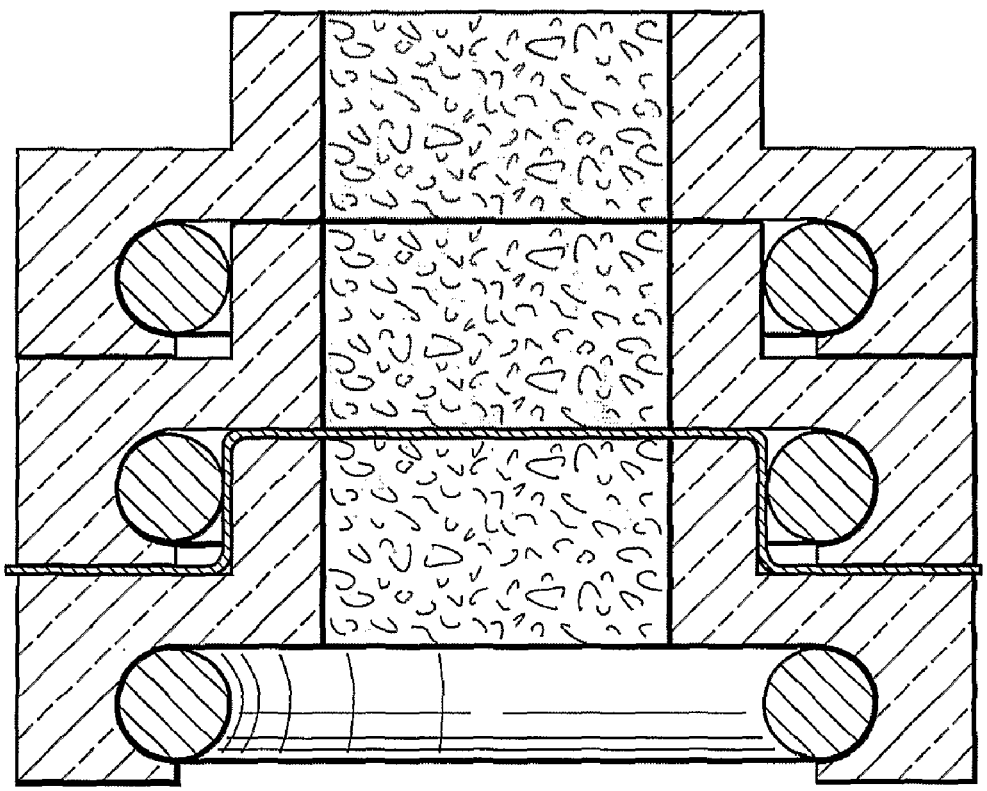
FIG. 6 shows a longitudinal cross-sectional view of three modules of a binding assay product according to a further embodiment.

The dried filters were loaded into custom VFI modules with a PVA film and mixer filters as shown in FIGS. 4, 5 and 6. More specifically, FIG. 4 shows a plan view of a mixing module (top right); a labelling module having a first binding component labelled with gold sol (left); and a capture module with a second binding component (bottom right).

FIG. 5 shows a side view of an assembled binding assay product, with the reagent modules stacked ready for application of the sample. From top to bottom the product comprises a lid, a sample well/wash buffer well, reagent filters with PVA film there between, a sump and a stand.

FIG. 6 shows a cross sectional view of assembled modules. For the purposes of this figure, part of the modules has been cut away to show a stack of three modules with a layer of PVA between the middles module and the bottom module (NB black deposits are due to the cutting).

Figure 7:
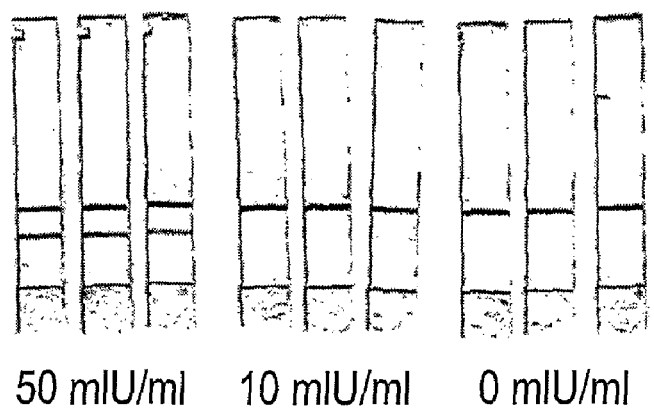
FIG. 7 is an image of test assay strips following testing of an embodiment.

Immunoassay conditions used 150 µl of urine sample spiked with purified hCG at 0, 10 and 50 mlU/ml and was subsequently applied to the sample module in the VFI system to reconstitute the dried reagents. For simplicity of communication the results were visualised using a standard pregnancy test assay strip (FIG. 7).

The upper pink band on the test strip functions as an assay control line, and captures the antibody conjugated to the gold particle directly. The lower band functions as an assay test line and the intensity of the formed band is proportional to the concentration of hCG present in the sample.

The data shows that the reagents have retained activity after drying into the frits (50 and 10 mlU/ml) with subsequent re-mobilisation and that there is negligible non specific binding (0 mlu/ml).

Example 2

Barriers on Flow Path

Figure 8:
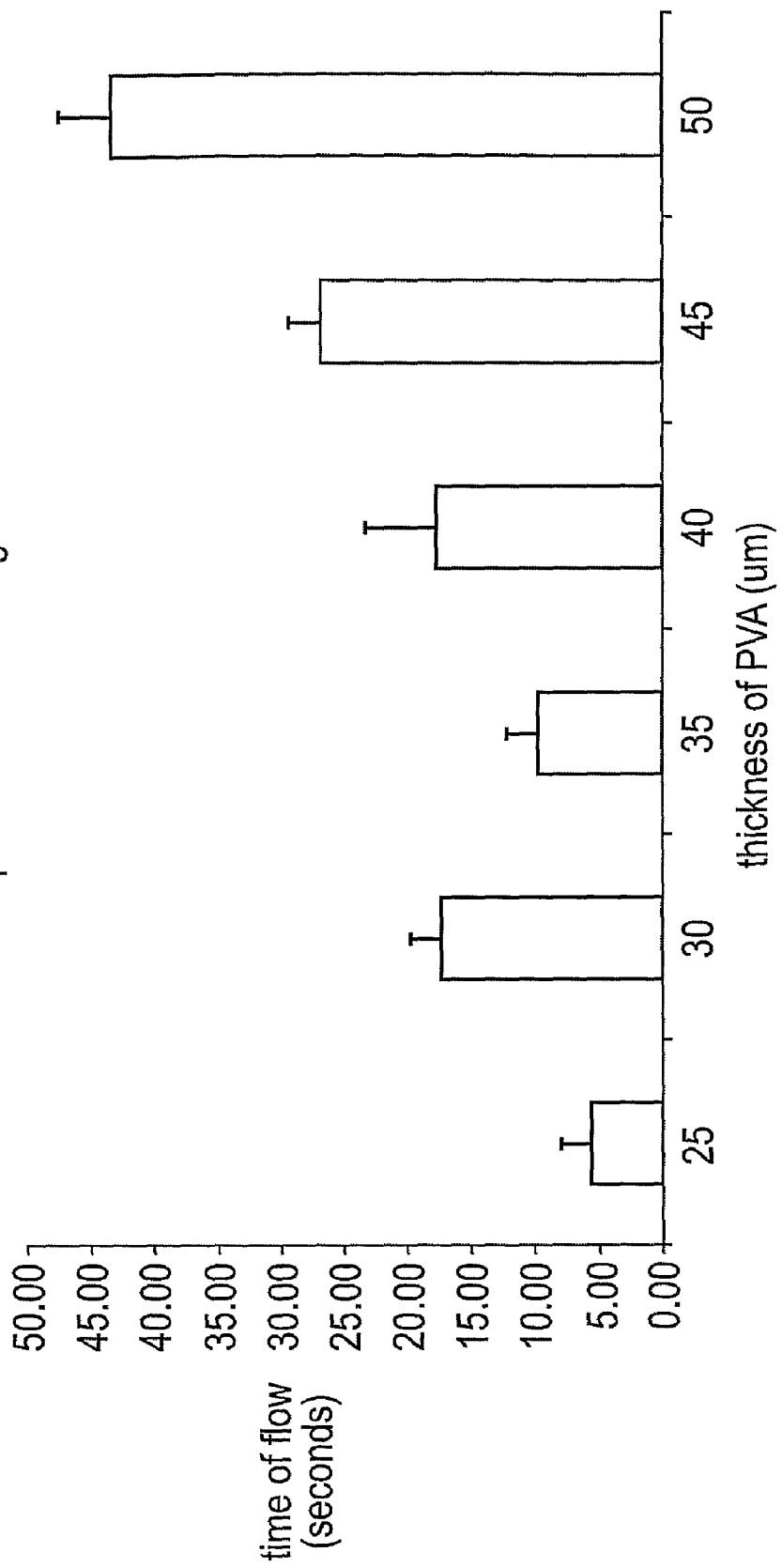
FIG. 8 is a graph showing time taken for liquid to pass through barriers on a flow path of one embodiment.
Figure 9:
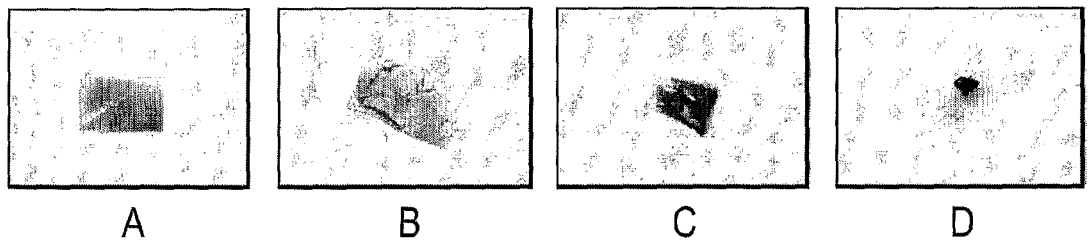
FIG. 9 shows four images (A to D) of PVA film dissolving in water over ~60 seconds.

PVA was made available in thicknesses ranging from 25 to 50 µm. These were assessed for dissolution time when disposed between two reagent frits. Pieces of film were held firmly between 2 Frits and 150 μl of coloured liquid added to the filter stack. The time taken for the liquid to colour the bottom filter was recorded and the results are shown as a graph in FIG. 8. FIG. 8 shows the variation in dissolution time and thus liquid to flow through filters separated by PVA film. This demonstrates that the thicker the PVA film is, the longer the liquid takes to flow through the filter stack.

Stacks of multiples of filters and films were also assembled and time for liquids to pass through the stacks was assessed. The data are shown in tables 1 and 2. CB134 and L712D are two types of PVA film (available from Monosol). CB134 is 35 μm thick. L712D is 70 μm thick (two 35 μm films were used in conjunction).

TABLE 1

Film dissolving times - Stack with Two dams

| $1^{st}$ dam film type | $1^{st}$ dam top filter | $1^{st}$ dam bottom filter | Time to break (sec) | $2^{nd}$ dam film type | $2^{nd}$ dam Top frit | $2^{nd}$ dam Bottom Frit | Mean Time to dissolve (seconds) |
|---|---|---|---|---|---|---|---|
| CB135 | F | F | 16.5 | CB135 | F | F | 30 |
| L712D | HP | HP | 103 | L712d | F | T | 44.7 |

T = 10 μm pore size frit, F = 30 μm pore size, and HP = 90 μm pore size.

TABLE 2

Film dissolving times - Stack with Three dams

| $1^{st}$ dam film type | $1^{st}$ dam top filter | $1^{st}$ dam bottom filter | Time to break (sec) | $2^{nd}$ dam film type | $2^{nd}$ dam Top frit | $2^{nd}$ dam Bottom Frit | Mean Time to break (seconds) | $3^{rd}$ dam film type | $3^{rd}$ dam top frit | $3^{rd}$ dam bottom frit | Time to break (seconds) |
|---|---|---|---|---|---|---|---|---|---|---|---|
| CB135 | HP | F | 21 | CB135 | F | F | 15 | CB135 | F | T | 14 |

T = 10 μm pore size frit, F = 30 μm pore size, and HP = 90 μm pore size

Example 3

PVA film was selected to be the soluble barrier material through research into many material types. PVA offers the optimal dissolution properties, with sufficient tensional strength and manufacture options (lamination, processing etc).

To indicate solubilisation of the film material, water was added to a section of 40 μm PVA film impregnated with a blue dye for visualisation. FIG. 9A-D are a series of pictures showing PVA (dyed blue for ease of visualisation) dissolving in water over a period of approximately 60 seconds.

Example 4

Sreptavidin was coupled to frits carrying an oxidised active chemistry and hetero-bifunctional coupling chemistry EDC/NHS. An immunoassay (described above) containing an antibody conjugated to biotin was captured on to the surface of the visualisation module in an antigen concentration dependent manner.

Figure 10:
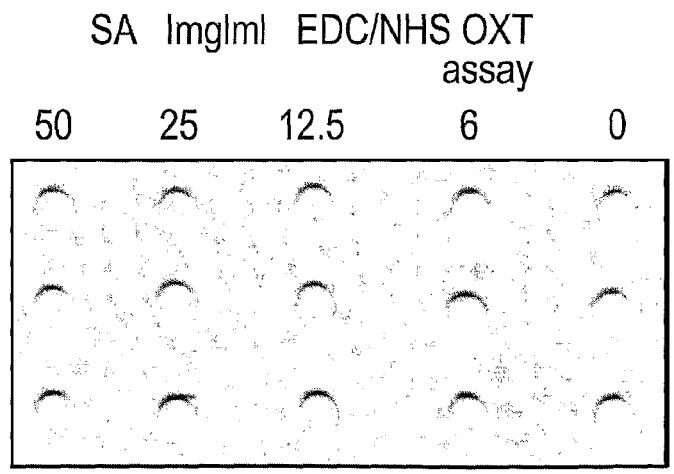
FIG. 10 shows an image of the capture of detection complexes via biotin on complex and streptavidin on frit material.

FIG. 10 shows the capture of detection complexes via biotin on complex and streptavidin on frit material. The figures shows the capture of such a complex of gold conjugate (specific to hCG) with decreasing concentrations of analyte, hCG (50, 25, 12.5, 6.25 and 0 mlU/ML) and a biotin labelled capture antibody (specific to hCG). The complex was captured via the binding pair of biotin on the complex and streptavidin on the filter. Visualisation was through the precipitation of gold sol.

Example 5

Figure 11:
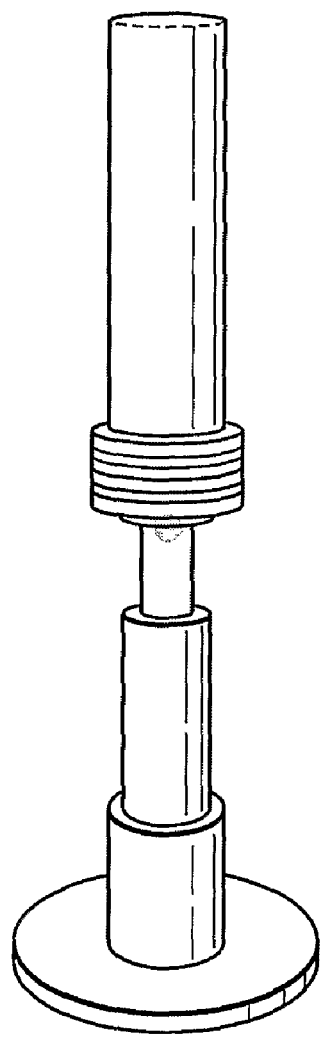
FIG. 11 shows a side view of a binding assay product in accordance with a further embodiment.

To assess the suitability of alternative detection module materials, a wet assay component system was developed and utilised sepharose activated with streptavidin held in an 'hour glass' modular system. Positive results were visualised as a pink red area where the complex has bound via biotin to the streptavidin in the upper area of the visualisation module. FIG. 11 shows and image of the wet assay with sepharose/streptavidin as the capture zone.

Example 6

Figure 12:
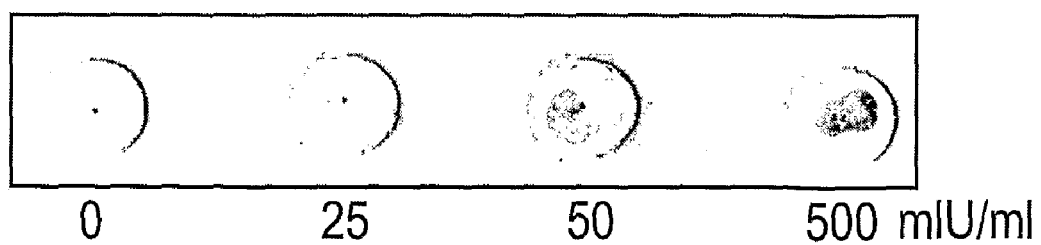
FIG. 12 shows an image of modules from a dried assay in accordance with another embodiment.

In this example a dried assay was produced with nitrocellulose as the visualisation module. Gold sol conjugate probe was dried into HP frits and stacked into a module with PVA film with F and T filters as a mixing zone. A piece of nitrocellulose treated with a specific hCG binding molecule was disposed immediately below the frit stack. Urine samples spiked with hCG at 0, 25, 50 and 500 mlU/ml were passed through the assay system. Where hCG was present a complex was captured in a dose dependent manner to the nitrocellulose (see FIG. 12).

Example 7

Figure 13:
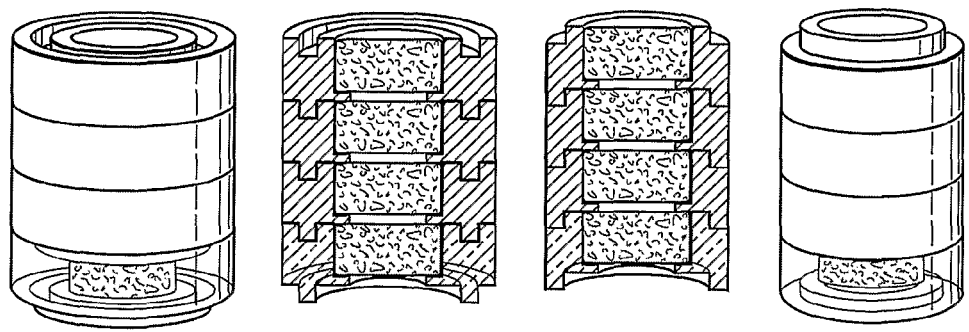
FIG. 13 is a perspective view of two binding assay products (each shown also with part cut away)
Figure 14:
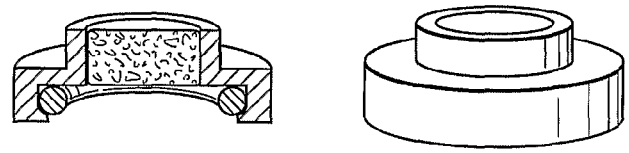
FIG. 14 is a perspective view of one module from a binding assay product (also shown with part cut away)
Figure 15:
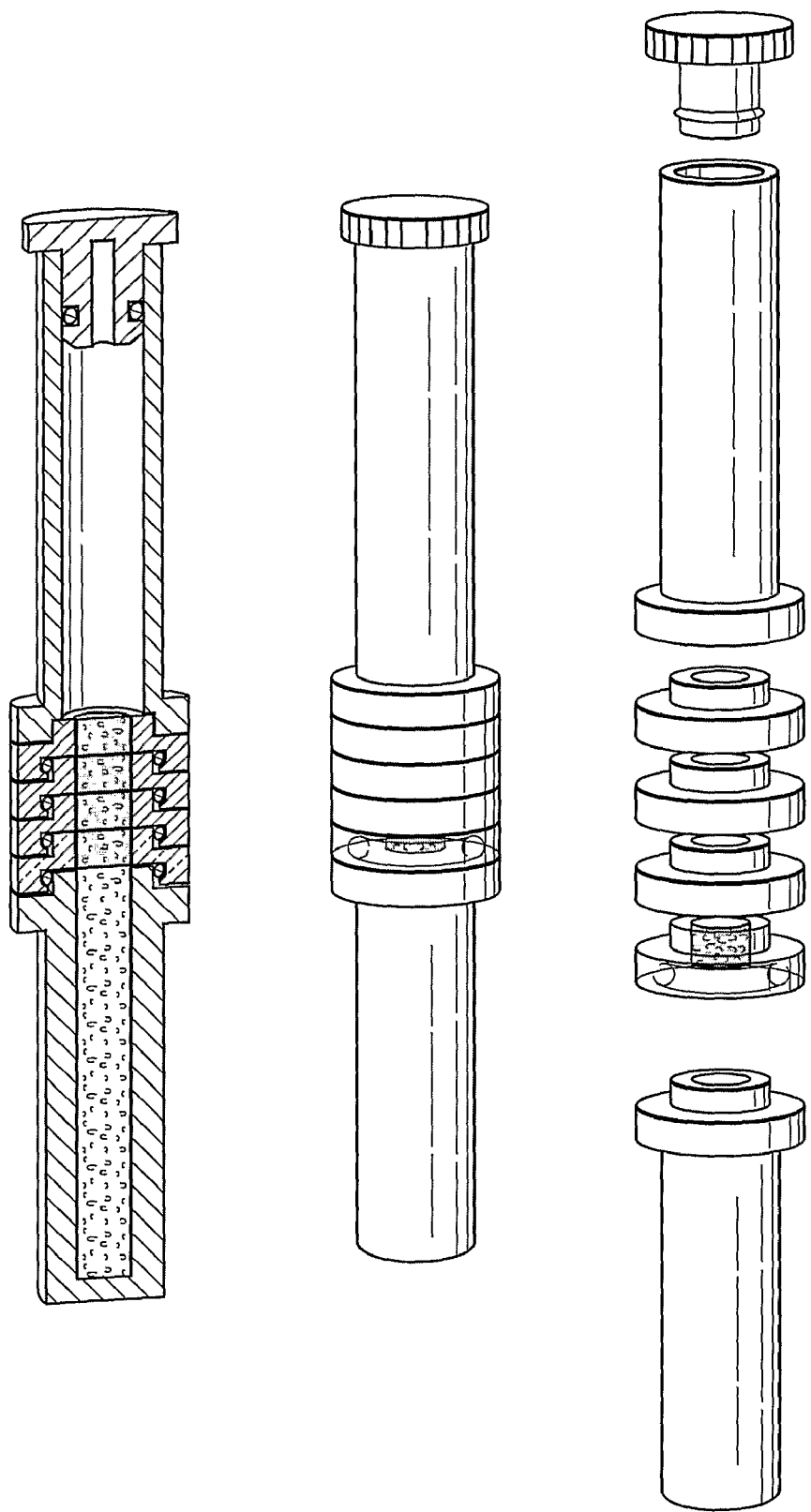
FIG. 15 is a perspective view of a binding assay product according to one embodiment (also shown with exploded view and with part cut away)
Figure 16:
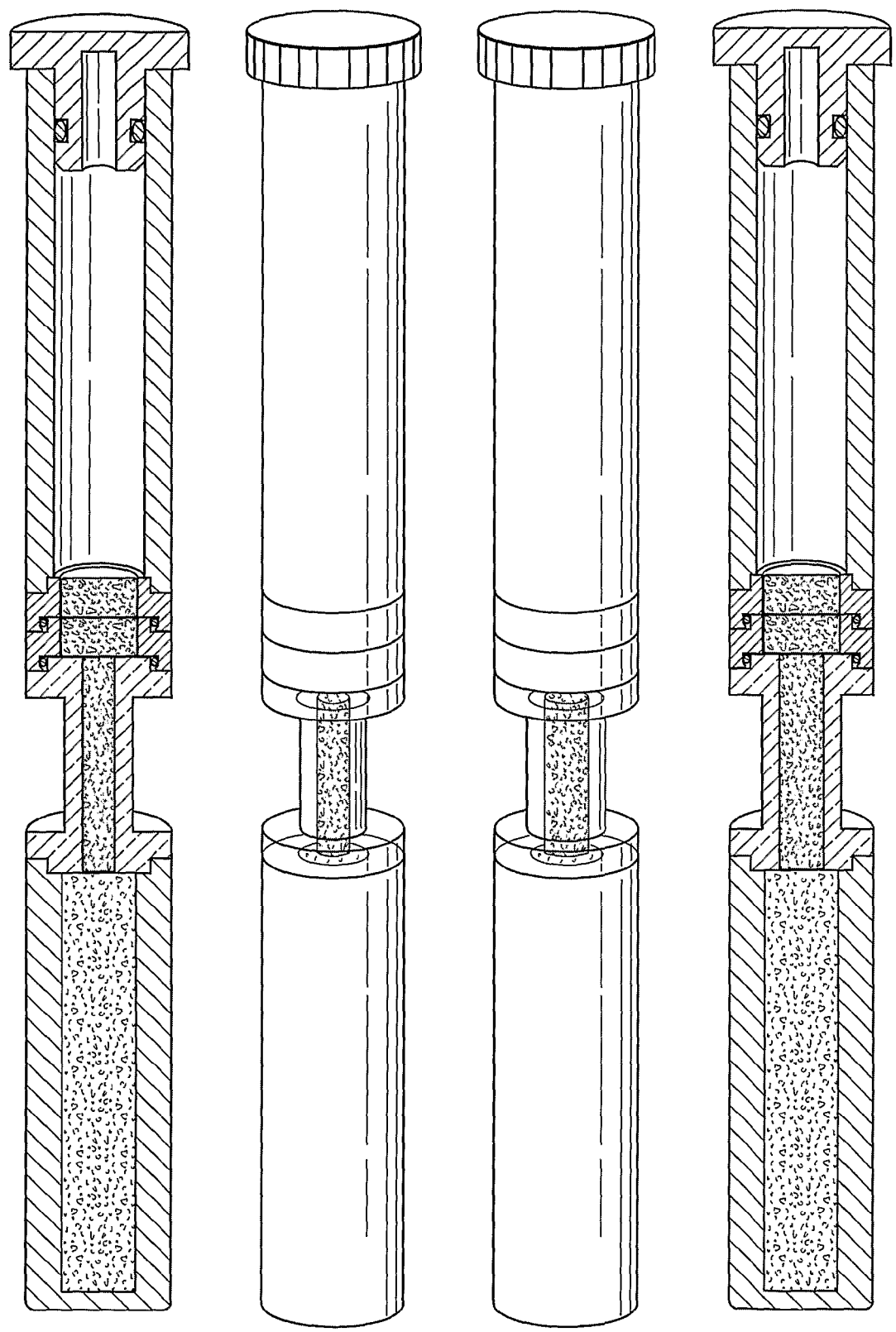
FIG. 16 is a perspective view of two binding assay products in accordance with further embodiments (each also shown with part cut away).

Examples of module configurations were prepared. FIG. 13 shows modules holding filters in a stack. FIG. 14 shows individual filter modules (one cut in half). FIG. 15 shows a complete binding assay product. FIG. 16 shows a complete binding assay product with an "hour glass" design for the visualisation zone.

The invention claimed is:

1. A binding assay product for detecting the presence of an analyte in a sample comprising:
    a labelling module comprising at least one first binding component capable of binding the analyte;
    a label connectable to the first binding component;
    a capture module comprising at least one second binding component capable of binding the analyte; and a visualisation module for detecting the first binding component connected to the label and bound to the second binding component via the analyte, wherein the capture, labelling and visualisation modules are independent modules and are interchangeably connectable with each other, wherein at least the labelling module and the capture module each comprise a fluid conducting medium comprising an open-porous structure in which the first and second binding components are embedded, and the labelling module, the capture module and the visualisation module together define a flow path, along which a sample is capable of flowing, and wherein the binding assay product further comprises at least one barrier along the flow path, the barrier carrying an assay reagent and being capable of delaying the progress of the sample along the flow path.

2. A binding assay product according to claim 1 wherein the barrier is soluble in water.

3. A binding assay product according to claim 1 wherein the at least one barrier interposes between the labelling module and the capture module and/or between the capture module and the visualisation module.

4. A binding assay product according to claim 1 wherein the visualisation module comprises a porous material to which the binding products are retained in the presence of an analyte.

5. A binding assay product according to claim 1 wherein the label is connected to the first binding component.

6. A binding assay product according to claim 5 wherein the first binding component is selected from the group consisting of avidin or biotin.

7. A binding assay product according to claim 1 and further comprising a mixing module, on the flow path, between the labelling module and the capture module.

8. A binding assay product according to claim 1 and further comprising a sample receiving module on the flow path comprising an absorbent material moving fluid by capillary action, in fluid communication with the labelling module.

9. A binding assay product according to claim 1 and further comprising a sump on the flow path, the sump comprising an absorbent material in fluid communication with the visualisation module.

10. A binding assay product according to claim 9 wherein the visualisation module comprises the boundary between the capture module and the sump.

11. A binding assay product according claim 1 and further comprising a casing around the labelling module, the capture module and the visualisation module.

12. A binding assay product according to claim 1 and further comprising a supply of a wash fluid.

13. A binding assay product according to claim 1 wherein the visualisation module comprises a blister which protrudes from the rest of the binding assay product.

14. A binding assay product according to claim 1 wherein the fluid flow path as defined by the visualisation module is narrower in cross section than the fluid flow path defined by the labelling module and/or the capture module.

15. A kit for making a binding assay product according to claim 1, the kit comprising the labelling module, the capture module and the visualisation module, the modules being interchangeably connectable with each other to form the flow path.

* * * * *

UNITED STATES PATENT AND TRADEMARK OFFICE
CERTIFICATE OF CORRECTION

| | | |
|---|---|---|
| PATENT NO. | : 8,241,588 B2 | |
| APPLICATION NO. | : 12/280245 | |
| DATED | : August 14, 2012 | |
| INVENTOR(S) | : Paul James Davis et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 265 days.

Signed and Sealed this
Fifteenth Day of January, 2013

David J. Kappos
*Director of the United States Patent and Trademark Office*

UNITED STATES PATENT AND TRADEMARK OFFICE
CERTIFICATE OF CORRECTION

PATENT NO. : 8,241,588 B2
APPLICATION NO. : 12/280245
DATED : August 14, 2012
INVENTOR(S) : Paul J. Davis et al.

It is certified that error appears in the above-identified patent and that said Letters Patent is hereby corrected as shown below:

In the Specifications

Column 2, Lines 4-5, replace "there are number ways" with --there are a number of ways--;

Line 35, replace "immunoassay". Such" with --immunoassay" (VFI). Such--;

Line 62, replace "lateral immunoassay" with --lateral flow immunoassay--.

Column 3, Line 27, replace "immuno assay" with --immunoassay--;

Line 45, replace "embedded" with --embedded.--.

Column 4, Line 36, replace "flow path" with --flow path.--;

Line 47, replace "polyvinyl alcohol" with --polyvinyl alcohol (PVA)--;

Line 51, replace "vertically rather then laterally" with --vertically rather than laterally--.

Column 6, Line 44, replace "end 4" with --end 4.--;

Line 66, replace "preferable" with --preferably--.

Column 7, Line 14, replace "sepharose" with --Sepharose--;

Line 17, replace "sepharose" with --Sepharose--;

Line 22, replace "sepharose" with --Sepharose--;

Line 62, replace "antibody (which" with --antibody (to which--.

Column 8, Line 1, replace "due" with --due to--;

Line 2, replace "sepharose" with --Sepharose--;

Line 15, replace "sepharose" with --Sepharose--;

Line 52, replace "sepharose" with --Sepharose--.

Column 9, Line 4, replace "sepharose" with --Sepharose--;

Line 40, replace "communication and from" with --communication to and from--.

Column 11, Line 32, replace "appropriately" with --appropriate--.

Signed and Sealed this
Twenty-first Day of May, 2013

Teresa Stanek Rea
*Acting Director of the United States Patent and Trademark Office*

CERTIFICATE OF CORRECTION (continued)
U.S. Pat. No. 8,241,588 B2

Column 12, Lines 24-25, replace "gonadotrophin" with --gonadotropin--;

Line 26, replace "sintered PE" with --sintered polyethylene (PE)--;

Line 45, replace "middles module" with --middle module--.

Column 13, Line 2, replace "2 Frits" with --2 frits--;

Line 56, replace "Sreptavidin" with --Streptavidin--;

Lines 63-64, replace "figures" with --figure--;

Line 66, replace "mlU/ML" with --mlU/ml--.

Column 14, Line 9, replace "sepharose" with --Sepharose--;

Line 13, replace "shows and" with --shows an--;

Line 13, replace "sepharose" with --Sepharose--.

In the Claims

Column 16, Claim 11, Line 15, replace "according claim 1" with --according to claim 1--.